US006829922B2

United States Patent
Patin et al.

(10) Patent No.: US 6,829,922 B2
(45) Date of Patent: Dec. 14, 2004

(54) EVALUATING FOAMED CEMENT UNDER PRESSURE AND TEMPERATURE

(75) Inventors: Ronald J. Patin, Lafayette, LA (US); Dennis W. Gray, Comanche, OK (US); James H. Cantrell, Duncan, OK (US); D. Chad Brenneis, Marlow, OK (US); Garland W. Davis, Comanche, OK (US); Wendell D. Riley, Marlow, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 102 days.

(21) Appl. No.: 10/255,124

(22) Filed: Sep. 25, 2002

(65) Prior Publication Data

US 2004/0055392 A1 Mar. 25, 2004

(51) Int. Cl.[7] .............................................. G01N 37/00
(52) U.S. Cl. ..................................................... 73/60.11
(58) Field of Search .............................. 73/64.41, 60.11, 73/54.01

(56) References Cited

U.S. PATENT DOCUMENTS

| | | | |
|---|---|---|---|
| 4,259,868 A | * 4/1981 | Rao et al. ..................... 73/597 |
| 4,648,264 A | 3/1987 | Freese et al. ................. 73/64.1 |
| 4,823,594 A | * 4/1989 | Gray .......................... 73/54.01 |
| 5,869,750 A | 2/1999 | Onan et al. ................. 73/64.41 |
| 6,345,535 B1 | 2/2002 | Sabins et al. ................. 73/818 |
| 6,367,550 B1 | 4/2002 | Chatterji et al. ............ 166/293 |
| 6,484,568 B1 | * 11/2002 | Griffith et al. ............. 73/60.11 |

* cited by examiner

*Primary Examiner*—Edward Lefkowitz
*Assistant Examiner*—T Miller
(74) *Attorney, Agent, or Firm*—John W. Wustenberg; Anthony L. Rahhal

(57) ABSTRACT

A test method for foamed cement does not transfer the test composition under pressure from one device to another and the equipment is not handled under dangerous pressure, thereby providing a safe test method. Steps include: rotating a paddle at a first speed in a pressurized foamable cement composition in a receptacle in a high pressure, high temperature chamber such that the foamable cement composition becomes a foamed cement; rotating the paddle at a second speed in the pressurized foamed cement for a selected time period; maintaining the foamed cement static after the selected time period and increasing temperature in the chamber during a foamed cement setting period; thereafter reducing temperature in the chamber and reducing pressure in the chamber; removing the foamed cement in a set condition and the paddle from the chamber; removing the set foamed cement from the paddle; and testing the removed foamed cement.

20 Claims, 1 Drawing Sheet

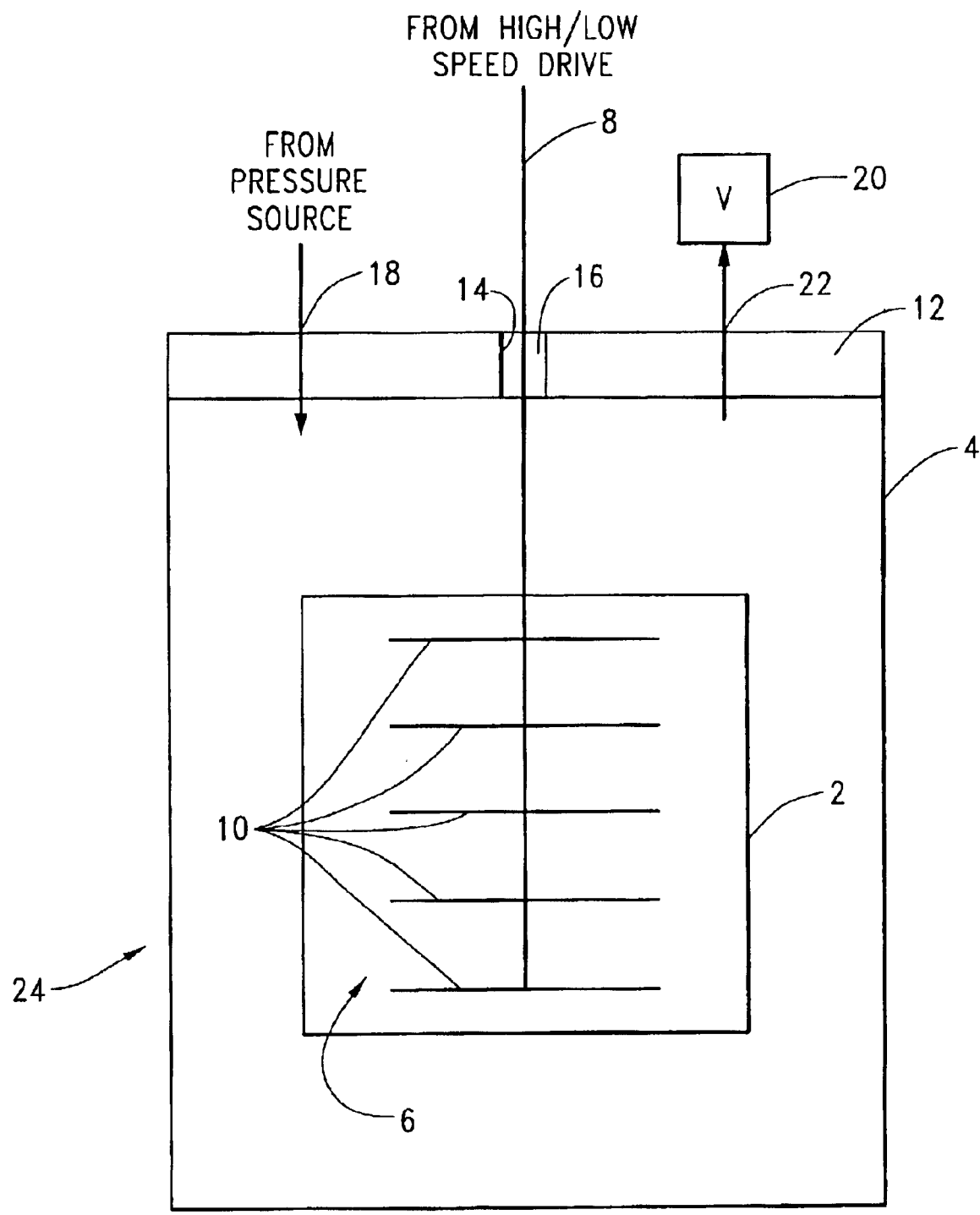

EVALUATING FOAMED CEMENT UNDER PRESSURE AND TEMPERATURE

BACKGROUND OF THE INVENTION

This invention relates generally to testing foamed cement, especially of types to be used in oil or gas wells.

Various compositions that are to be used in wells are preferably tested before they are used so that the nature of the composition can be known, thereby to determine whether the composition might function as desired down in the high pressure, high temperature environment often encountered in an oil or gas well, for example. Foamed cement is a particular type of composition that is used downhole and that preferably is tested before use. Although the desirability of knowing characteristics of compositions has been known, there is a continuing need for improved methods and devices for testing such compositions, including in particular foamed cement.

SUMMARY OF THE INVENTION

A prior type of foamed cement testing has called for the material under test to be transferred under pressure from one device to another. The present invention provides a test method for foamed cement in which there is no transfer of the test composition under pressure from one device to another and in which the equipment is not handled under dangerous pressure, thereby providing a safe test method.

The present invention can be defined as a method of evaluating a foamed cement of a type for use in a well, comprising: rotating a paddle at a first speed in a pressurized foamable cement composition in a receptacle in a high pressure, high temperature chamber such that the foamable cement composition becomes a foamed cement; rotating the paddle at a second speed in the pressurized foamed cement for a selected time period; maintaining the foamed cement static after the selected time period and increasing temperature in the chamber during a foamed cement setting period; thereafter reducing temperature in the chamber and reducing pressure in the chamber; removing the foamed cement in a set condition and the paddle from the chamber; removing the foamed cement in the set condition from the paddle; and testing the removed foamed cement in the set condition.

Another definition of the present invention is as a method of evaluating a foamable cement of a type for use in an oil or gas well, comprising: rotating a paddle at a first speed in pressurized foamable cement disposed in a receptacle in a high pressure, high temperature chamber and continuing rotating until the foamable cement is foamed cement; rotating the paddle at a second speed in the pressurized foamed cement for a selected pump-in time period defined for a cementing job to use the same type of composition as the foamed cement; maintaining the foamed cement static after the selected time period and increasing temperature in the chamber to a selected wellbore temperature for a setting time period such that the foamed cement becomes set cement; slowly reducing temperature in the chamber below the selected wellbore temperature and slowly reducing pressure in the chamber after the setting time period; removing the set cement and the paddle from the chamber after the temperature and pressure are reduced; removing the set cement in pieces from the paddle; and testing each of the pieces of the removed set cement.

Other and further objects, features, and advantages of the present invention will be readily apparent to those skilled in the art when the following description of the preferred embodiments is read in conjunction with the accompanying drawing.

BRIEF DESCRIPTION OF THE DRAWINGS

The drawing schematically represents a high pressure, high temperature device that can be used in implementing the method of the present invention.

DETAILED DESCRIPTION OF THE INVENTION

Referring to the drawing, a foamable cement composition of selected design to be tested is placed in a suitable receptacle 2, such as a slurry cup capable of withstanding pressure up to about 500 pounds per square inch (psi) and temperature up to about 400° F. Such a receptacle 2 is made of a suitable material, one example of which is stainless steel of a type used in test equipment in the oil and gas industry as known in the art.

The slurry cup or other suitable receptacle 2 with the foamable cement composition to be tested is placed, in an unfoamed state, in a high pressure, high temperature chamber 4, such as provided by an autoclave of a type used in test equipment in the oil and gas industry as known in the art. A paddle 6, such as of a type used in test equipment in the oil and gas industry as known in the art, is placed in the composition in the receptacle 2, and a paddle shaft 8 extending from paddle blades 10 extends through a removable lid 12 having an aperture 14 through which the paddle shaft 8 extends. The lid 12 is appropriately attached to the body of the chamber 4, and the lid 12 has suitable packing 16, such as of known type, for maintaining a high pressure seal between the lid 12 and the chamber 4 and paddle shaft 8.

The interior of the chamber 4 is pressurized, such as up to 500 psi. Pressurization can be implemented in any suitable manner, one known manner of which includes connecting a high pressure nitrogen source to an inlet into the chamber 4, such as through a port 18 defined through the lid 12 of the chamber 4.

A high speed motor, such as from a conventional electric drill, for example, is connected to the paddle shaft 8, such as by conventionally attaching the chuck of the drill to the external end of the paddle shaft 8. The paddle 6 is rotated at high speed, such as up to 2,000 revolutions per minute (rpm), to foam the composition. Once the composition is foamed, thereby providing foamed cement, the high speed motor in one implementation of the method is disconnected and a lower speed motor connected, such as for example one of known type capable of rotating the paddle 6 at a speed up to about 150 rpm per American Petroleum Institute (API) standards.

Such lower speed rotation of the paddle 6 is continued preferably for an amount of time equivalent to the period of time the actual-use composition is to be pumped to place it downhole in an actual well. For example, such circulating might continue for about forty minutes to one and one-half hours or more, depending on the particular desired pumping schedule. Preferably this would continue in accordance with API protocol.

Once the lower speed circulating time has elapsed, rotating the paddle 6 is stopped to allow the foamed cement to become static as it would in an actual well. During this time, the temperature in the chamber 4 is increased as desired for the test, such as to be comparable to what the temperature is expected to be in an actual well. Under these conditions, the foamed cement begins to set.

Thereafter, temperature and pressure are reduced. Preferably, it is cooled slowly and pressure released slowly, such as for example by slightly opening a relief valve 20 connected to a port 22 in the lid 12 to permit pressure reduction over a period of time, such as two hours or so, for example. Notwithstanding any existing applicable test standard to the contrary, such cooling and pressure release are carried out sufficiently to allow personnel to safely handle test device 24.

Once the material has suitably cooled and sufficient pressure reduction has occurred, the lid 12 of the chamber 4 is removed and separated from the paddle shaft 8. The foamed cement in a set condition is removed from the receptacle 2, which removal may be enhanced by using a slurry cup having a shape that facilitates extraction (for example, by having the cup sides taper outwardly from bottom to top). The removed paddle 6 with the set foamed cement hardened on it is positioned in such a manner as to facilitate cutting the set foamed cement into pieces of appropriate size to be tested. For example, the set foamed cement with the embedded paddle 6 is placed horizontally on a table such that the paddle 6 is parallel to, and secured on, the supporting surface of the table. The set foamed cement placed on the table is cut (using a known cutting device, for example) into four pieces, for example, with each piece being marked as to its position (for example, top, bottom, middle top, middle bottom). The density or other characteristic of each such piece is determined in any suitable manner, such as known techniques appropriate for use in making laboratory density measurements of set foamed cement in the oil and gas industry. The characteristic of the overall piece can also be determined using a composite of the individual piece characteristics as known in the art.

Thus, the foregoing provides a test method for foamed cement in which there is no transfer of the test composition under pressure from one device to another and in which the equipment is not handled under dangerous pressure, thereby providing a safe test method.

Accordingly, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A method of evaluating a foamed cement of a type for use in a well, comprising the steps of:

rotating a paddle at a first speed in a foamable cement composition in a receptacle in a pressurized chamber such that the foamable cement composition becomes a foamed cement;

rotating the paddle at a second speed in the foamed cement for a selected time period;

maintaining the foamed cement static after the selected time period and increasing temperature in the chamber during a foamed cement setting period;

thereafter reducing temperature and pressure in the chamber;

removing the foamed cement in a set condition and the paddle from the chamber; and removing the foamed cement in the set condition from the paddle.

2. The method of claim 1 further comprising the step of testing the removed foamed cement in the set condition.

3. The method of claim 1 wherein the first speed is up to about 2,000 revolutions per minute.

4. The method of claim 1 wherein the second speed is up to about 150 revolutions per minute.

5. The method of claim 1 wherein the selected time period is between about forty minutes and about ninety minutes.

6. The method of claim 1 wherein the chamber is pressurized up to about 500 pounds per square inch.

7. The method of claim 1 wherein the chamber is pressurized using nitrogen.

8. The method of claim 1 wherein the temperature in the chamber during the foamed cement setting period is up to about 400° F.

9. The method of claim 1 wherein the step of reducing temperature and pressure in the chamber occurs over an about two hour time period.

10. A method of evaluating a foamable cement of a type for use in an oil or gas well, comprising the steps of:

rotating a paddle at a first speed in a foamable cement disposed in a receptacle in a pressurized chamber and continuing rotating until the foamable cement is a foamed cement;

rotating the paddle at a second speed in the foamed cement for a selected pump-in time period defined for a cementing job using the same type of composition as the foamed cement;

maintaining the foamed cement static after the selected pump-in time period and increasing temperature in the chamber to a selected wellbore temperature for a setting time period such that the foamed cement becomes set cement;

reducing temperature in the chamber below the selected wellbore temperature and reducing pressure in the chamber after the setting time period;

removing the set cement and the paddle from the chamber after the temperature and pressure are reduced; and removing the set cement in pieces from the paddle.

11. The method of claim 10 further comprising the step of testing each of the pieces of the removed set cement.

12. The method of claim 10 wherein the first speed is up to about 2,000 revolutions per minute.

13. The method of claim 10 wherein the second speed is up to about 150 revolutions per minute.

14. The method of claim 10 wherein the setting time period is between about forty minutes and about ninety minutes.

15. The method of claim 10 wherein the chamber is pressurized up to about 500 pounds per square inch.

16. The method of claim 10 wherein the chamber is pressurized using nitrogen.

17. The method of claim 10 wherein the selected wellbore temperature is up to about 400° F.

18. The method of claim 10 wherein the step of reducing temperature in the chamber below the selected wellbore temperature and reducing pressure in the chamber after the setting time period occurs over an about two hour time period.

19. A method of evaluating a foamable cement of a type for use in a well, comprising the steps of:

providing a foamable cement composition in a receptacle in a chamber;

pressurizing the chamber;

rotating a paddle at a first speed in the foamable cement composition until the foamable cement composition becomes a foamed cement;

rotating the paddle at a second speed slower than the first speed in the foamed cement for a selected time period;

ceasing rotating the paddle in the foamed cement after the selected time period to allow the foamed cement to set during a foamed cement setting period;

increasing temperature in the chamber during the foamed cement setting period;

thereafter reducing temperature and pressure in the chamber; and removing the set foamed cement and the paddle from the chamber.

20. The method of claim 19 further comprising the step of removing the set foamed cement from the paddle.

* * * * *